(12) United States Patent
Simandan et al.

(10) Patent No.: US 9,309,271 B2
(45) Date of Patent: Apr. 12, 2016

(54) PREPARATION OF ISOCYANATO SILANES

(71) Applicant: Momentive Performance Materials GmbH, Leverkusen (DE)

(72) Inventors: Tiberiu L. Simandan, Termoli (IT); Roland Wagner, Bonn (DE); Holger J. Glatzer, Leverkusen (DE); Karl-Heinz Sockel, Leverkusen (DE); Karl-Heinz Stachulla, Leverkusen (DE); Christian Wenske, Solingen (DE)

(73) Assignee: Momentive Performance Materials GmbH, Leverkusen (DE)

( * ) Notice: Subject to any disclaimer, the term of this patent is extended or adjusted under 35 U.S.C. 154(b) by 18 days.

(21) Appl. No.: 14/402,140

(22) PCT Filed: May 28, 2013

(86) PCT No.: PCT/US2013/042845
§ 371 (c)(1),
(2) Date: Nov. 19, 2014

(87) PCT Pub. No.: WO2013/181136
PCT Pub. Date: Dec. 5, 2013

(65) Prior Publication Data
US 2015/0133682 A1     May 14, 2015

Related U.S. Application Data

(60) Provisional application No. 61/652,507, filed on May 29, 2012.

(51) Int. Cl.
*C07F 7/10* (2006.01)
*C07F 7/18* (2006.01)

(52) U.S. Cl.
CPC ............. *C07F 7/1844* (2013.01); *C07F 7/1836* (2013.01)

(58) Field of Classification Search
CPC ........................................................ C07F 7/18
USPC ........................................................ 556/414
See application file for complete search history.

(56) References Cited

U.S. PATENT DOCUMENTS

| | | |
|---|---|---|
| 3,528,977 A | 9/1970 | Schnettler |
| 4,193,932 A | 3/1980 | Yamamoto et al. |
| 4,528,195 A | 7/1985 | Thorogood |
| 4,654,428 A * | 3/1987 | Kurashima ............ C07F 7/1892 556/414 |
| 4,870,198 A | 9/1989 | Mormann et al. |
| 5,739,327 A | 4/1998 | Arbogast et al. |
| 6,352,993 B1 | 3/2002 | Lee et al. |
| 7,060,849 B1 | 6/2006 | Childress et al. |
| 7,217,777 B2 | 5/2007 | Lange et al. |
| 2007/0173640 A1 | 7/2007 | Park et al. |
| 2009/0092923 A1 | 4/2009 | Hayashi |
| 2010/0305085 A1 | 12/2010 | Thede et al. |
| 2011/0198030 A1 | 8/2011 | Burckhardt |

FOREIGN PATENT DOCUMENTS

| | | |
|---|---|---|
| DE | 4140448 | 6/1993 |
| EP | 2 305 765 A1 | 4/2011 |

OTHER PUBLICATIONS

International Search Report (PCT/US2013/042845), mailed Aug. 30, 2013.*
M. R. Angelastro et. al., "Inhibition of Human Neutrophil Elastase with Peptidyl Electrophilic Ketones, 2. Orally Active PG-Val-Pro-Val Pentafluoroethyl Ketones", J. Med. Chem., 1994, vol. 37, pp. 4538-4553.
R. S. Lodhi et. al., "Synthesis and biological activity of 2-(substituted aryl)-3-(N1-imidazolyl-acetamidyl)-4-oxo-thiazolidines and their 5-arylidine derivatives", Indian J. Chem., 1998, vol. 37B, pp. 899-903.
J. Pielichowski et. al., "Trichloroethylene in Organic Synthesis: II. Reaction of Trichloroethylene with Secondary Amines", Tetrahedron, 1984, vol. 40, No. 14, pp. 2671-2675.

* cited by examiner

*Primary Examiner* — Porfirio Nazario Gonzalez
*Assistant Examiner* — Kofi Adzamli
(74) *Attorney, Agent, or Firm* — James C. Abruzzo

(57) ABSTRACT

A process for the preparation of alkoxysilyl group-containing isocyanate compounds which includes the step of reacting carbonyl chloride ClC(=O)Cl with an alkoxysilyl group-containing amine in the presence of a high boiling point base, and optionally in the presence of an inert organic solvent, in order to minimize by product production and to simplify product purification, is disclosed.

19 Claims, No Drawings

PREPARATION OF ISOCYANATO SILANES

CROSS REFERENCE TO RELATED APPLICATIONS

The present application claims priority to U.S. Provisional Application No. 61/652,507 filed May 29, 2012, which is herein incorporated by reference in its entirety.

FIELD OF THE INVENTION

The present invention relates to the production of isocyanato silanes. In particular, the present invention relates to the production of alkoxysilyl group-containing isocyanates by a process comprising reacting an alkoxysilyl group-containing amine with carbonyl chloride in the presence of at least one tertiary amino-containing compound having a high boiling point, and optionally in the presence of an inert organic solvent.

BACKGROUND OF THE INVENTION

Organic isocyanates have widespread industrial uses. One method of manufacture of most commercial isocyanates involves the reaction of amine precursors with carbonyl chloride. During the process, carbamoyl chlorides are formed first which decompose to provide the desired isocyanates. Typically, for each mole of isocyanate group created, two molar equivalents of hydrogen chloride are generated. Once generated, hydrogen chloride may react with the functional groups in the amine precursors, the intermediates and the isocyanate products generating various byproducts. In the case of the preparation of alkoxysilyl group-containing isocyanates, hydrogen chloride, upon generation, reacts with the alkoxysilyl groups in the isocyanate products, generating chlorosilanes and the corresponding alcohols, which leads to the formation of further side products, thus lowering the overall yield of the target isocyanates.

In an effort to solve the problem, U.S. Pat. No. 4,654,428 discloses the use of tertiary amines such as triethyl or tripropyl amines in the reaction mixture. In the process, hydrogen chloride is neutralized by the tertiary amines forming amine hydrochloride salts, which precipitate and are subsequently filtered off. The isocyanate product is obtained by distillation of the filtrate.

However, there are a number of disadvantages associated with this process. Firstly, the amine salts formed from the '428 tertiary amines and hydrogen chloride are typically a high volume, low density, and fluffy solid, which is difficult and expensive to handle. Secondly, the distilled product made from the process disclosed in the '428 patent can be contaminated with the amine hydrochloride salts dissolved in the filtrate and/or hydrogen chloride formed by dissociation of the amine salts. To obviate the disadvantages, the '428 patent discloses treating the filtrate or the distillate with an alkali metal or alkaline earth metal salt of a carboxylic acid. This additional treatment step adds costs to the process. Thirdly, in practice, to ensure the efficient quenching of the hydrogen chloride, excess amine is used, which leads to an additional step of stripping off the excess amine from the final product, thus further adding costs to the process.

Accordingly, there is a continuing need in the isocyanato silane manufacturing industry for an enhanced process to produce the desired products without the additional steps and shortfalls of the prior art processes.

SUMMARY OF THE INVENTION

In one aspect, there is provided a process for the preparation of an alkoxysilyl group-containing isocyanate compound having the general Formula (I):

$$(R^1O)_{3-a}R^2{}_aSi-R^3-NCO \qquad (I)$$

wherein
each $R^1$ is independently a branched or straight chain alkyl or cycloalkyl group of from 1 to 6 carbon atoms;
each $R^2$ is independently a branched or straight chain alkyl or cycloalkyl group of from 1 to 6 carbon atoms;
$R^3$ is a branched or straight chain alkylene or cycloalkylene group of from 1 to 12 carbon atoms, an arylene group of from 6 to 10 carbon atoms, or an aralkylene group of from 7 to 10 carbon atoms; and
a is 0, 1 or 2.

The process comprises:
(i) reacting carbonyl chloride, $ClC(=O)Cl$, with a corresponding alkoxysilyl group-containing amine having the general Formula (II):

$$(R^1O)_{3-a}R^2{}_aSi-R^3-NH_2 \qquad (II)$$

wherein
each $R^1$ is independently a branched or straight chain alkyl or cycloalkyl group of from 1 to 6 carbon atoms;
each $R^2$ is independently a branched or straight chain alkyl or cycloalkyl group of from 1 to 6 carbon atoms;
$R^3$ is a branched or straight chain alkylene or cycloalkylene group of from 1 to 12 carbon atoms, an arylene group of from 6 to 10 carbon atoms, or an aralkylene group of from 7 to 10 carbon atoms; and
a is 0, 1 or 2,
in the presence of a tertiary amino-containing compound having the general Formula (III):

$$R^4R^5NR^6O-[CH_2CH_2O-]_x[CH_2CH(CH_3)O-]_y[C_4H_8O-]_zR^7-X \qquad (III)$$

wherein
each $R^4$ is independently a straight or branched chain alkyl, cycloalkyl, alkenyl, aryl, aralkyl or arenyl group up to 18 carbon atoms, a heterocarbon group containing from 2 to 18 carbon atoms and at least one oxygen or $(-)_2NR^8$ group, wherein $R^8$ is a straight or branched chain alkyl, cycloalkyl, akenyl, aryl, aralkyl or arenyl group from 1 to 10 carbon atoms, or a group in which $R^4$ has a chemical bond with $R^5$ to form a cyclic structure containing the nitrogen atom;
each $R^5$ is independently a straight or branched chain alkyl, cycloalkyl, alkenyl, aryl, aralkyl or arenyl group containing up to 18 carbon atoms, a heterocarbon group containing from 2 to 18 carbon atoms and at least one oxygen or $(-)_2NR^8$ group, wherein $R^8$ is a straight or branched chain alkyl, cycloalkyl, akenyl, aryl, aralkyl or arenyl group from 1 to 10 carbon atoms, or a group in which $R^5$ has a chemical bond with $R^4$ to form a cyclic structure containing the nitrogen atom; $R^6$ is a straight or branched alkylene group of from 1 to 10 carbon atoms, a cycloalkylene or arylene group of from 5 to 10 carbon atoms, or a $-R^9C(=O)-$ group wherein $R^9$ is a straight or branched alkylene group of from 1 to 10 carbon atoms, a cycloalkylene group of from 5 to 10 carbon atoms or an arylene group of from 1 to 10 carbon atoms;
$R^6$ is a straight or branched alkylene group of from 1 to 10 carbon atoms, a cycloalkylene or arylene group of from 5 to 10 carbon atoms, or a $-R^9C(=O)-$ group wherein $R^9$ is a straight or branched alkylene group of from 1 to 10 carbon atoms, a cycloalkylene group of from 5 to 10 carbon atoms or an arylene group of from 1 to 10 carbon atoms;

$R^7$ is a straight or branched alkylene group of from 1 to 10 carbon atoms, a cycloalkylene or arylene group of from 5 to 10 carbon atoms, or a —(O═C—)$R^9$— group wherein $R^9$ is a straight or branched alkylene group of from 1 to 10 carbon atoms, a cycloalkylene group of from 5 to 10 carbon atoms or an arylene group of from 1 to 10 carbon atoms;

X is hydrogen or a —NR$^4$R$^5$ group, wherein $R^4$ and $R^5$ have the same meanings as above;

x is 0 to 50;

y is 0 to 50; and z is 0 to 50, with the proviso that the sum of x+y+z is from 2 to 100, to provide for an alkoxysilyl group-containing isocyanate compound having the general Formula (I):

$$(R^1O)_{3-a}R^2_aSi—R^3—NCO \qquad (I)$$

wherein each $R^1$ is independently a branched or straight chain alkyl or cycloalkyl group of from 1 to 6 carbon atoms;

each $R^2$ is independently a branched or straight chain alkyl or cycloalkyl group of from 1 to 6 carbon atoms;

$R^3$ is a branched or straight chain alkylene or cycloalkylene group of from 1 to 12 carbon atoms, an arylene group of from 6 to 10 carbon atoms or an aralkylene group of from 7 to 10 carbon atoms;

(ii) separating the hydrochloride salt tertiary amino-containing compound from the alkoxysilyl group-containing isocyanate compound of step (i), and optionally, (iii) purifying the alkoxysilyl group-containing isocyanate of step (ii).

DETAILED DESCRIPTION OF THE INVENTION

The present invention provides a process for the preparation of an alkoxysilyl group-containing isocyanate compound having the general Formula (I):

$$(R^1O)_{3-a}R^2_aSi—R^3—NCO \qquad (I)$$

wherein each $R^1$ is independently a branched or straight chain alkyl or cycloalkyl group of from 1 to 6 carbon atoms;

each $R^2$ is independently a branched or straight chain alkyl or cycloalkyl group of from 1 to 6 carbon atoms;

$R^3$ is a branched or straight chain alkylene or cycloalkylene group of from 1 to 12 carbon atoms, an arylene group of from 6 to 10 carbon atoms or an aralkylene group of from 7 to 10 carbon atoms; and a is 0, 1 or 2.

The alkoxysilyl group-containing isocyanate compounds of Formula (I) are prepared by reacting carbonyl chloride ClC(═O)Cl with an alkoxysilyl group-containing amine of Formula (II):

$$(R^1O)_{3-a}R^2_aSi—R^3—NH_2 \qquad (II)$$

wherein each $R^1$ is independently a branched or straight chain alkyl or cycloalkyl group of from 1 to 6 carbon atoms;

each $R^2$ is independently a branched or straight chain alkyl or cycloalkyl group of from 1 to 6 carbon atoms;

$R^3$ is a branched or straight chain alkylene or cycloalkylene group of from 1 to 12 carbon atoms, an arylene group of from 6 to 10 carbon atoms or an aralkylene group of from 7 to 10 carbon atoms; and a is 0, 1 or 2.

Exemplary alkoxysilyl group-containing amines include but are not limited to 3-trimethoxysilylpropylamine, 3-triethoxysilylpropylamine, 3-tripropoxysilylpropylamine, 3-tributoxysilylpropylamine, 1-trimethoxysilylmethylamine, 1-dimethoxymethylsilylmethylamine, 1-diethoxymethylsilylmethylamine, 3-dimethoxymethylsilylpropylamine, and 3-diethoxymethylsilylpropylamine.

In one embodiment, $R^1$ is methyl or ethyl group, $R^2$ is methyl, $R^3$ is methylene, ethylene or propylene and "a" is 0 or 1. In another embodiment, $R^1$ is methyl or ethyl group, $R^3$ is propylene and "a" is 0.

In another embodiment, the molar ratio of the amino groups of the alkoxysilyl group containing amine to the chloride groups of carbonyl chloride, $H_2N/Cl$, is from 0.4 to 0.6, more specifically from 0.48 to 0.52, and even more specially 0.5. In the molar ratio of $H_2N/Cl$, the carbonyl chloride contributes 2 chlorine atoms.

In another embodiment, tertiary amino-containing compound having the general Formula (III):

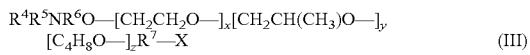

$$R^4R^5NR^6O—[CH_2CH_2O—]_x[CH_2CH(CH_3)O—]_y$$
$$[C_4H_8O—]_zR^7—X \qquad (III)$$

wherein each $R^4$ is independently a straight or branched chain alkyl, cycloalkyl, alkenyl, aryl, aralkyl or arenyl group up to 18 carbon atoms, a heterocarbon group containing from 2 to 18 carbon atoms and at least one oxygen or (—)$_2$NR$^8$ group, wherein $R^8$ is a straight or branched chain alkyl, cycloalkyl, akenyl, aryl, aralkyl or arenyl group from 1 to 10 carbon atoms, or a group in which $R^4$ has a chemical bond with $R^5$ to form a cyclic structure containing the nitrogen atom;

each $R^5$ is independently a straight or branched chain alkyl, cycloalkyl, alkenyl, aryl, aralkyl or arenyl group up to 18 carbon atoms, a heterocarbon group containing from 2 to 18 carbon atoms and at least one oxygen or (—)$_2$NR$^8$ group, wherein $R^8$ is a straight or branched chain alkyl, cycloalkyl, akenyl, aryl, aralkyl or arenyl group from 1 to 10 carbon atoms, or a group in which $R^5$ has a chemical bond with $R^4$ to form a cyclic structure containing the nitrogen atom;

$R^6$ is a straight or branched alkylene group of from 1 to 10 carbon atoms, a cycloalkylene or arylene group of from 5 to 10 carbon atoms, or a —$R^9$C(═O)— group wherein $R^9$ is a straight or branched alkylene group of from 1 to 10 carbon atoms, a cycloalkylene group of from 5 to 10 carbon atoms or an arylene group of from 1 to 10 carbon atoms;

$R^7$ is a straight or branched alkylene group of from 1 to 10 carbon atoms, a cycloalkylene or arylene group of from 5 to 10 carbon atoms, or a —(O═C—)$R^9$— group wherein $R^9$ is a straight or branched alkylene group of from 1 to 10 carbon atoms, a cycloalkylene group of from 5 to 10 carbon atoms or an arylene group of from 1 to 10 carbon atoms;

X is hydrogen or a —NR$^4$R$^5$ group, wherein $R^4$ and $R^5$ have the same meanings as above;

x is 0 to 50;

y is 0 to 50; and z is 0 to 50, with the proviso that the sum of x+y+z is from 2 to 100, more specifically 3 to 50 and still more specifically 5 to 15.

In one embodiment, the tertiary amino-containing compound of Formula (III) has a boiling point of at least 250° C., and more specifically, a boiling point of from 300° C. to 500° C. at 760 mm Hg pressure. The tertiary amino-containing compound reacts with the hydrogen chloride generated from the reaction of the carbonyl chloride with alkoxysilyl-containing amine compound to form a hydrochloride salt with the tertiary amino-containing compound. The hydrochloride salt of the tertiary amino-containing compound is either a solid melting at a temperature below 150° C., and more specifically below 75° C., a viscous paste at 25° C. or a liquid at 25° C. Advantageously, the tertiary amino-containing compound is employed in an amount of from 0.95 mole to about five moles per mole of hydrogen chloride generated. Preferably a molar excess of tertiary amino-containing compound is employed relative to the molar amount of hydrogen chloride generated. When the hydrochloride salt of the tertiary amino-containing compound is a solid melting at a temperature below 150° C., the reaction mixture of step (i) can be heated to a temperature above the melting point of the hydrochloride salt of the tertiary amino-containing compound thereby melting the hydrochloride salt of the tertiary amino-containing compound to form a liquid. The melt of the hydrochloride salt of the tertiary amino-containing compound avoids absorption of the alkoxysilyl group-containing isocyanate compound into the salts and therefore provides for more efficient separation of hydrochloride salt with the tertiary amino-containing compound from the alkoxysilyl group-containing isocyanate compound in step (ii).

In another embodiment, the hydrochloride salt of the tertiary amino-containing compound is insoluble or has a low solubility of less than 2 weight percent of hydrochloride salt of the tertiary amino-containing compound in the alkoxysilyl group-containing isocyanate compound at 25° C. or in a mixture comprising the alkoxysilyl group-containing isocyanate compound and an organic solvent. The insolubility or low solubility of the hydrochloride salt of the tertiary amino-containing compound aids in the separation of the salt from the alkoxysilyl group-containing isocyanate compound during step (ii).

Representative and non-limiting examples of $R^4R^5N-$ are $(CH_3)_2N-$, $(CH_3CH_2)_2N-$, $(CH_3CH_2CH_2)_2N-$, $[(CH_3)_2CH]_2N-$, $(CH_3)N-$,

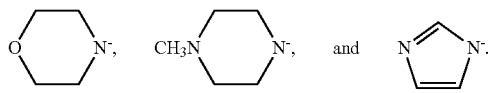

It is within the scope of the invention to incorporate polyether moieties that are derived from at least one monomer selected from ethylene oxide, propylene oxide and butylene oxide monomers which form a composition with the tertiary amino-containing compound of Formula (III).

Still another aspect of the present invention provides the process for the preparation of alkoxysilyl group-containing isocyanate compound of the general Formula (I) wherein the tertiary amino-containing compound of Formula (III) is preferably selected from the group consisting of

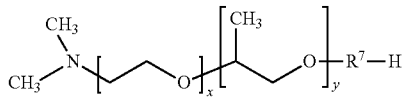
(IV)

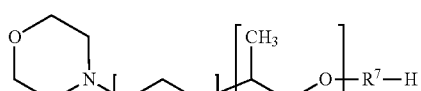
(V)

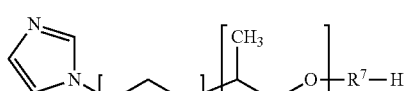
(VI)

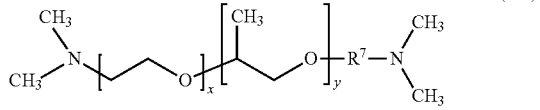
(VII)

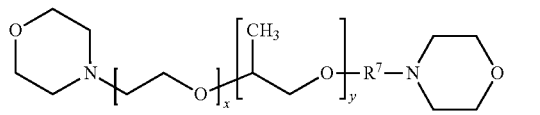
(VIII)

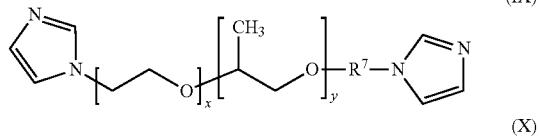
(IX)

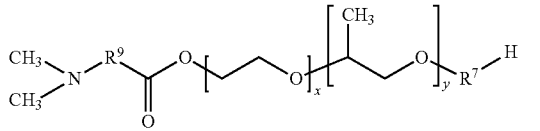
(X)

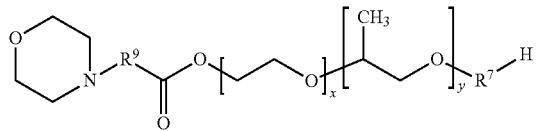
(XI)

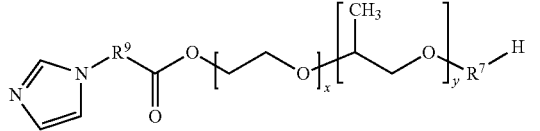
(XII)

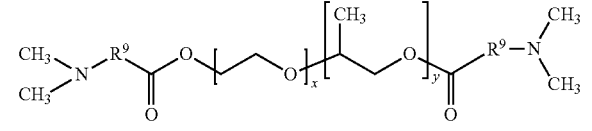
(XIII)

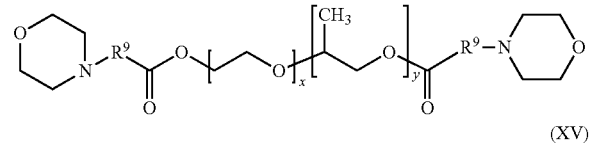
(XIV)

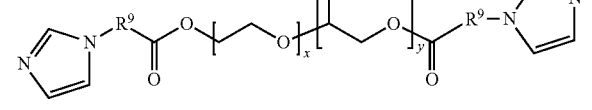
(XV)

wherein in each of formulae (IV)-(XV):

$R^7$ is a straight or branched alkylene group of from 1 to 6 carbon atoms, a cycloalkylene or arylene group of 6 carbon atoms, specifically C1 to C3 alkylene, such as $-CH_2CH_2-$, $-CH_2CH_2CH_2-$, or $-CH_2CH(CH_3)-$;

$R^9$ is a straight or branched alkylene group of from 1 to 6 carbon atoms, a cycloalkylene or an arylene group of from 6 carbon atoms, specifically C1 to C3 alkylene, such as $-CH_2CH_2-$, $-CH_2CH_2CH_2-$, or $-CH_2CH(CH_3)-$;

each x and y is independently from 0 to 50, specifically from 0 to 10, more specifically from 0 to 5, most specifically from 0 to 3, especially from 0 to 2, provided that the sum of x and y is from 2 to 100, specifically from 3 to 25, more specifically from 3 to 15, most specifically from 3 to 10, especially from 3 to 5. Mixtures of two or more tertiary amino-containing compound of Formula (IV) to (XV) can be used.

The synthesis of tertiary amino-containing compounds which contain aromatic moieties (imidazole) or more complex ether bridges are known. For example, U.S. Pat. No. 5,739,327 describes the synthesis of morpholine modified polyethers. US 2007/173640 and DE 2903653 describe the synthesis of imidazole modified ethers and polyethers.

Without wishing to be bound by any particular theory, it is believed that the incorporation of the ethylene oxide, propylene oxide or butylene oxide moieties into the structure of the tertiary amino-containing compound represented by the structures above attributes to the low melting and high boiling point feature of these bases. In some embodiments, the low melting high boiling point bases have a melting point of less than 100° C., preferably less than 30° C., and have boiling points of at least 250° C. measured at (atmospheric pressure) 760 mm Hg pressure.

The synthesis of tertiary amino bases containing ester structures is known. Illustratively, U.S. Pat. No. 3,528,977 and U.S. Pat. No. 6,352,993 describe the synthesis of morpholine modified ester derivatives starting from bromo acetic acid esters. DE 4140448 describes the synthesis of morpholine modified ester derivatives starting from the corresponding chloro acetic acid ester precursors.

The synthesis of morpholine derivatives containing tert-butyl ester structures is known too and has been described by M. R. Angelastro et. al. in Journal of Med. Chem., 1994, vol. 37, 4538-4553.

The synthesis of imidazole modified ester derivatives starts from chloro acetic acid esters (R. S. Lodhi et. al., Indian J. of Chem., Section B, Organic Chemistry incl. Medical Chem., 1998, vol. 37, 899-903) or bromo acetic acid esters (US 2010/305085, example 40a).

One way to prepare tertiary amino-containing compounds of Formula (III) which also contain an ester functional group is by reacting a compound containing at least one tertiary amino function and one primary or secondary alcohol function with carboxylic acid esters, for example

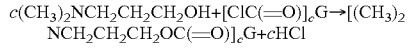

wherein G is —R$^{10}$[CH$_2$CH$_2$O—]$_x$[CH$_2$CH(CH$_3$)O—]$_y$[C$_4$H$_8$O-]$_z$R$^{10}$—, where R$^{10}$ is denotes a straight or branched alkylene group of from 1 to 10 carbon atoms, a cycloalkylene or arylene group of from 5 to 10 carbon atoms, wherein R$^{10}$ can contain an oxygen atom, c is 1 or 2, x is 0 to 50, y is 0 to 50 and z is 0 to 50, with the proviso that the sum of x+y+z=2 to 100, followed by removal of the amine hydrochloride and optionally further neutralization of the residue amine hydrochloride salt with a strong base, such as alkali or alkaline salts of hydroxide or alkoxide.

The synthesis of tertiary amino-containing compound which also contain an ester functional group can be made by starting from secondary amines which are reacted with chloro carboxylic acid esters. In a specific embodiment, chloroacetic acid chloride, chloropropionic acid chloride and reacted with a polyether containing one to two hydroxyl groups to produce chloroacetic acid esters or chloropropionic acid esters. These esters are then reacted in an excess of a secondary amine (i.e. morpholine) yielding the target compounds by amination of the CH$_2$Cl moiety, followed by neutralization of the amine hydrochloride salts (J. Pielichowski et. al., Tetrahedron, 1984, vol. 40, 2671-2676).

In yet another way to prepare tertiary amino-containing compound of Formula (III) is by reacting a compound containing at least one secondary amino function with polyether containing a chloro group, as for example

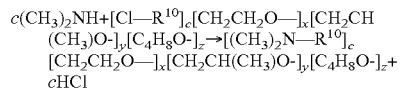

wherein R$^{10}$ is denotes a straight or branched alkylene group of from 1 to 10 carbon atoms, a cycloalkylene or arylene group of from 5 to 10 carbon atoms, and wherein R$^{10}$ optionally contains an oxygen atom, c is 1 or 2, x is 0 to 50, y is 0 to 50 and z is 0 to 50, with the proviso that the sum of x+y+z=2 to 100, followed by removal and the amine hydrochloride and optionally further neutralization of the residue amine hydrochloride salt with a strong base, such as alkali or alkaline salts of hydroxide or alkoxide.

Any organic solvent inactive to the reactants and the product can be used as an inert solvent in the process of the present invention. Suitable solvents include but are not limited to hydrocarbons such as benzene, toluene, n-hexane or cyclohexane; halogenated hydrocarbons such as methylene chloride, chloroform or trichloroethylene; ethers such as ethyl ether, 1,2-diethoxy ethane or dioxane; esters such as methyl acetate or ethyl acetate; and mixtures of two or more thereof.

The processes of the invention to prepare alkoxysilyl group-containing isocyanate having the general Formula (I) are carried out at a temperature of −50° C. to 150° C., and more specially −15° C. to 50° C. After completion of the reaction, the high boiling point base hydrochloride salts advantageously settle at the bottom of the reactor, as a liquid, paste or as a low melting solid.

The reaction mixture containing the target isocyanate compound(s) can be separated from the hydrochloride salts of the tertiary amino-containing compounds of Formula (III) by centrifugation, decantation or filtration. The final products, isocyanate(s) of Formula (I), can be obtained from the decant or filtrate by distillation. The hydrochloride salts of the tertiary amino-containing compounds that remain in the reactor can be treated with a base to recycle the tertiary amine-containing compound of Formula (III).

In another embodiment, the hydrochloride salts of the tertiary amino-containing compounds can be neutralized to form inorganic chloride salts, which are then separated from the mixture before distillation.

Removing hydrochloride salts of the tertiary amino-containing compounds by phase separation ensures that the crude alkoxysilyl-containing isocyante product contains a reduced amount of chloride salts. In one embodiment, the crude alkoxysilyl-containing isocyanate product compositions contain low levels of the hydrochloride salts of the tertiary amino-containing compounds, specifically, the chloride level is less than 2000 parts per million chloride, more specifically less than 500 parts per million chloride, and even more specifically, less than 100 parts per million chloride, based on the weight of the alkoxysilyl-containing isocyanate compound, after the separation step (ii). When this low chloride containing crude alkoxysilyl-containing isocyanate compound is further purified, such as by distillation, the resulting alkoxysilyl-containing isocyanate compound is characterized by an advantageously low number of silylchloride groups, thus providing a low chloride content that is less than 1000 parts per million chloride, advantageously less than 100 parts per million chloride, and more advantageously less than 10 parts per million chloride, based on the weight of the alkoxysilyl-containing isocyanate compound.

In one embodiment, the hydrochloride salts tertiary amino-containing compound can be neutralized and then recycled (reused) in step (i) of another batch to prepare the alkoxysilyl group-containing isocyanate compound or continuously recycled into step (i) of a continuous process for preparing an alkoxysilyl group-containing isocyanate compound. The recycling of the tertiary amino-containing compound after being neutralized improves the overall cost of the process by eliminating the need to use newly purchased tertiary amino-containing compounds, and decreases the amount of waste that would result from the process if the hydrochloride salts of the tertiary amino-containing compounds were not recycled and just handled as a waste product.

In still another embodiment, the process can be run in a batch process or a continuous process.

In another embodiment, the present invention relates to products made by all of the processes of the invention described above. The products include alkoxysilyl group-containing isocyanate compound(s) represented by Formula (I) described herein above. Non-limiting examples of the alkoxysilyl group-containing isocyanate compounds include but are not limited to 3-isocyanatopropyltrimethoxysilane, 3-isocyanatopropyltriethoxysilane, and 1-isocyanatomethyl-trimethoxysilane. In one embodiment, the products contain high boiling tertiary amines or high boiling low melting bases described herein above and/or salts thereof.

The following examples are intended to illustrate, but in no way limit the scope of the present invention. All parts and percentages are by weight and all temperatures are in degrees Celsius unless explicitly stated otherwise.

EXAMPLES

Comparative Example A

In a 1000 mL three-necked flask, equipped with a reflux condenser, a thermometer, a dropping funnel and a mechanical stirrer, morpholine (453 grams, 5 moles amine) and propylene glycol monomethyl ether (200 grams) were mixed at room temperature and heated to reflux (130° C.).

Next, ClCH$_2$CH$_2$OCH$_2$CH$_2$OCH$_2$CH$_2$Cl (187 grams, 2 moles as Cl groups) was added to the flask over 30 minutes. The solution turned turbid and was maintained at reflux (140° C.) for one hour. Afterwards, the mixture was cooled to room temperature and the morpholine hydrochloride salt was filtered off. The filter cake was washed twice with 100 ml propylene glycol monomethyl ether. Volatiles were removed from the combined liquid phases at 90° C./5 mbar. From the remaining liquid phase some additional salt precipitated visibly. 30 ml propylene glycol monomethyl ether was added and the mixture filtered once again. Volatiles were removed at 90° C./5 mbar to yield 258 grams of a yellow-brownish oily morpholine derivative of the structure

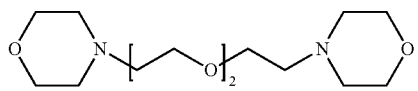

$^1$H-NMR confirmed the structure.

Comparative Example B

In a 2000 mL three-necked flask, equipped with a reflux condenser, a thermometer, a dropping funnel and a mechanical stirrer, ethanol (800 grams) was heated to reflux. Sodium metal (67.2 grams, 2.94 moles) was added and reacted with the ethanol within 6 hours. Imidazole (202 grams, 2.97 moles) was added and the mixture maintained at reflux for 1 hour. Then ClCH$_2$CH$_2$OCH$_2$CH$_2$Cl (210 grams, 2.94 moles as Cl) was added over 20 minutes and the mixture maintained at reflux for 7 hours.

Afterwards, the mixture was cooled to room temperature and the sodium chloride filtered off. The filter cake was washed twice with 100 mL ethanol. Volatiles were removed from the combined liquid phases at 70° C./S mbar to provide 317 g of a brownish oil. $^1$H-NMR showed that the oil consisted 85% of imidazole derivative of the structure

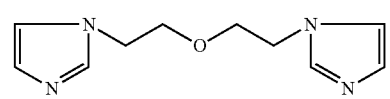 [SMILES: c1cn(CCOCCn2ccnc2)cn1]

and high boiling ethoxy ethers of diethylene glycol.

Comparative Example C

In a 2000-ml three-necked flask, equipped with a reflux condenser, a gas outlet to the exhaust system, a thermometer, a dropping funnel and a mechanical stirrer, dipropylene glycol monomethyl ether (209 grams, 1.41 moles), triethylamine (213 grams, 2.1 mole) and n-hexane (500 ml) were mixed. The mixture was cooled to 15° C. and SOCl$_2$ (250 grams, 2.1 moles) was added over 1 hour. The temperature increased to 32° C. The dark cake like mixture was further diluted with 100 ml n-hexane and heated to 70-80° C. for 2.5 hours. The cake like material was cooled to room temperature and the triethylamine hydrochloride filtered off. The filter cake was washed twice with 150 ml n-hexane. The combined n-hexane extracts were distilled twice to provide 126.3 g of a colorless liquid of the structure

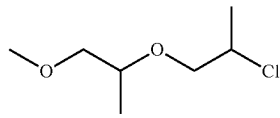

b.p. 72-74° C./18 mmHg $^1$H-NMR confirmed the structure.

In a 1000-ml three-necked flask, equipped with a reflux condenser, a thermometer, a dropping funnel and a mechanical stirrer, dipropylene glycol monomethyl ether (200 grams) was heated to 120° C. Sodium (11.5 grams, 0.5 mole) was added and reacted with the dipropylene glycol monomethyl ether within 1 hour. The mixture was cooled to 80° C. and imidazole (34 grams, 0.5 mole) was added. The mixture was heated to 120° C. for 2.5 hours. Afterwards, the halogenated ether

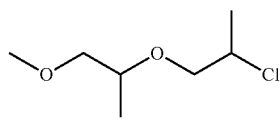

(83.3 grams, 0.5 mole Cl) was added over 45 minutes and the mixture maintained at 120° C. for 8 hours. Afterwards, the mixture was cooled to room temperature and the NaCl filtered off. Volatiles are removed from the liquid phase at 70° C./10 mbar to provide 53 g of a brownish oily imidazole derivative of the structure

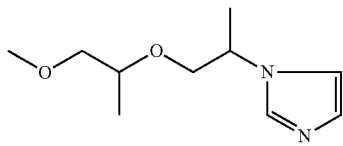

$^1$H-NMR showed that the product consisted of the target structure (80%) and high boiling dipropylene glycol monomethyl ether condensates.

Comparative Example D

In a 500-ml three-necked flask, equipped with a reflux condenser, a thermometer, a dropping funnel and a mechanical stirrer, morpholine (52.3 grams, 0.6 mole amine) and the halogenated ether

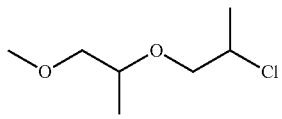

(10 grams, 0.06 mole as Cl) were mixed at room temperature and heated to 120° C. for 10 hours. The product was cooled to room temperature and 200 grams of a 50% active aqueous NaOH solution was added. The phases separated. The aqueous phase was extracted with 50 ml toluene. The oil phase and the toluene extract were combined. Volatiles were removed at 90° C./10 mbar to provide 12 grams of a brownish oily morpholine derivative of the structure

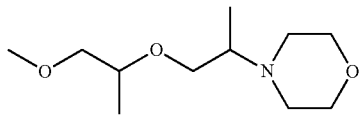

$^1$H-NMR confirmed the structure.

Example 1

A chloroacetic acid ester of the structure

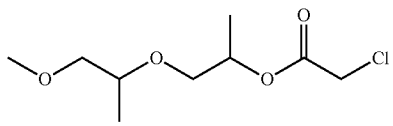

was prepared by placing into a reaction vessel dipropylene glycol monomethyl ether (331 grams, 2.24 mol) at room temperature under nitrogen. Over a span of one hour, chloroacetic acid chloride (279 grams, 2.46 mol) is added dropwise, with intense stirring. During the dropwise addition, the temperature increased and an hydrogen chloride formed. Upon completion of the dropwise addition, the batch is heated to 130° C. for 30 minutes. All constituents boiling at up to 130° C./20 hPa were then removed through a distillation. The result product was of a light yellow oil.

A 500-ml three-necked flask equipped with refluxing condenser, thermometer, dropping funnel and mechanical stirrer was charged with (111 grams, 1.33 mole as amine) of morpholine and (30 grams, 0.133 mole) of chloro acetic acid ester of the structure

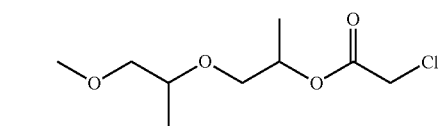

The temperature increased to 85° C. The mixture was cooled to room temperature then stirred at room temperature for 12 hours. Upon cooling morpholine hydrochloride precipitated. The salt was filtered off and the filter cake was washed with 50 ml butyl acetate. Volatiles were removed from the combined liquid phases at 60° C./10 mbar. From the remaining liquid phase some additional salt precipitated visibly. Additional butyl acetate (30 grams) was added and the mixture was filtered once again. Volatiles were removed at 60° C./10 mbar.

The reaction yielded 31 grams of a transparent yellow oily morpholine derivative of the structure

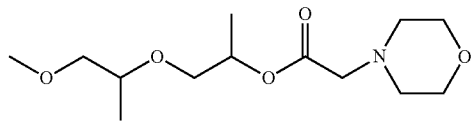 [SMILES: COCC(C)OCC(C)OC(=O)CN1CCOCC1]

$^1$H-NMR confirmed the complete conversion of the —CH$_2$Cl moiety and the formation of the target structure.

The morpholine ester derivative prepared above (0.5 gram) was mixed vigorously with 2.5 g of a 30% active aqueous NaOH solution. Both materials were left in contact to each other for 6 hours. The morpholine ester derivative completely separated from the NaOH solution within approximately 5 minutes and formed a transparent yellow top phase. A $^1$H-NMR of a sample from the organic top phase taken after 6 hours confirmed that the structure of the morpholine derivative did not change.

Example 2

Tripropylene glycol (431 grams, 2.24 moles) are placed at room temperature under nitrogen. Over a span of one hour, chloroacetic acid chloride (558 grams, 4.93 moles) are added dropwise, with intense stirring. During the dropwise addition, the temperature rises to 82° C., and an intensive formation of HCl sets in. Upon completion of the dropwise addition, the batch is heated to 130° C. for 30 minutes. All constituents boiling at up to 130° C./20 hPa are then removed via distillation. The result is a light yellow oil.

A 250-ml three-necked flask, equipped with refluxing condenser, thermometer, dropping funnel and mechanical stirrer, was charged with morpholine (34.8 grams, 0.4 mole amine), 2-propanol (50 ml), and a chloro acetic acid ester prepared above with the structure

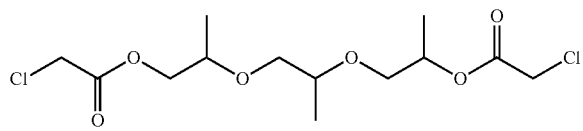 [SMILES: CC(COC(=O)CCl)OCC(C)OCC(C)OC(=O)CCl]

(5.28 grams, 0.04 mole as Cl). The mixture was stirred at room temperature for 12 hours. Morpholine hydrochloride started to precipitate after approximately one hour. The salt was filtered off and the volatiles were removed at 70° C./10 mbar. A slurry consisting of an oil phase and a salt phase was obtained. This slurry was washed first with 50 ml n-hexane and afterwards with 50 ml butyl acetate. Volatiles were removed from the n-hexane and butyl acetate extracts at 60° C./10 mbar.

The reaction yielded 6.5 grams of a transparent yellow oily morpholine derivative of the structure

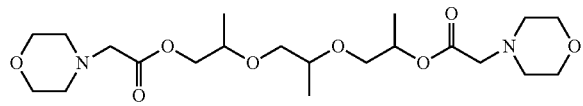 [SMILES: CC(COC(=O)CN1CCOCC1)OCC(C)OCC(C)OC(=O)CN1CCOCC1]

$^1$H-NMR confirmed the complete conversion of the —CH$_2$Cl moiety and the formation of the target structure.

The morpholine ester derivative above was mixed vigorously with 2.5 grams of a 30% active aqueous NaOH solution. Both materials were left in contact to each other for 6 hours. The morpholine ester derivative completely separated from the NaOH solution within approximately 10 minutes and formed a transparent yellow top phase. A $^1$H-NMR of a sample taken from the organic top phase after 6 hours confirmed that the structure of the morpholine derivative did not change. At the interphase between the top oil phase and the bottom NaOH phase a very minor portion of a white waxy material was observed.

Example 3

A 500-ml three-necked flask, equipped with refluxing condenser, thermometer, dropping funnel and mechanical stirrer, was charged with morpholine (264 grams, 3.2 mole amine) at room temperature. Chloroacetic acid ester of the structure

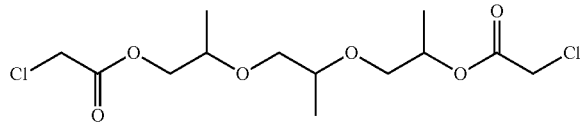 [SMILES: CC(COC(=O)CCl)OCC(C)OCC(C)OC(=O)CCl]

(138 grams, 0.8 mole as Cl), that was prepared in accordance with the procedure of Example 2, was added during 40 minutes. The temperature increased to 95° C. and was maintained there for two hours. Morpholine hydrochloride started to precipitate after approximately 0.5 hours. The salt was filtered off and washed with a hydrocarbon fraction (boiling point range 60-100° C.). Target product and hydrocarbon fraction were unified and volatiles removed at 70° C./20 mbar. An oil phase was obtained which contained some visible salt traces. The oil phase was mixed with 50 ml of the hydrocarbon fraction, filtered and the volatiles were removed in vacuum. This process was repeated in total five times.

The obtained crude product was mixed with 100 grams of a 50 wt % active aqueous NaOH solution. The tertiary amine separated from the NaOH solution within 10 minutes. The phases were separated and the tertiary amine mixed with 100 grams of a 30 wt % active aqueous NaCl solution. The phases separated within 10 minutes. This washing process using the NaCl solution was repeated in total five times. Yield 68.1 grams of a yellow to brownish oil. $^1$H-NMR confirmed the complete conversion of the —CH$_2$Cl moiety and the formation of the target structure.

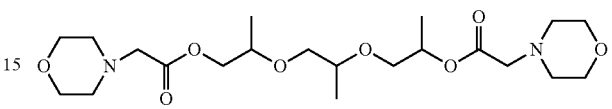

Example 4

A 250 ml three-necked flask, equipped with refluxing condenser, thermometer, dropping funnel and mechanical stirrer was charged with the tertiary amine derivative

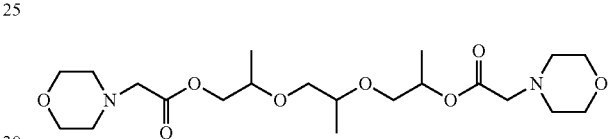

(68.1 grams, 0.3 mole as N) and CH$_3$OCH$_2$CH(CH$_3$)OH (27.5 grams, 0.3 mole as OH) at room temperature. Lauric acid chloride (60.1 grams, 0.274 mole) was added during 30 minutes. The temperature increased to 80° C. A viscous slurry containing the amine salt solution and an ester of the structure

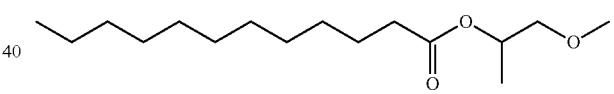

was obtained. The excess on CH$_3$OCH$_2$CH(CH$_3$)OH was removed at 65° C./10 mm. The non-volatile portion was cooled to 30° C.

The data indicate that the hydrochloride salt of the tertiary amino-containing compound, which formed during the preparation of the lauric acid ester was a viscous slurry (paste-like substance) and not a fluffy, a high melting amine hydrochloride salt.

Isocyanatopropyltrimethoxysilane (62 grams, 0.3 mole) was added to the mixture prepared above. This mixture was subjected to a vacuum distillation over a 15-cm Vigreux column. The maximum temperature of the distillation bottle was set to 160° C. Two colorless fractions were obtained and subsequently analyzed by means of 1H-NMR and elemental analysis.

| fraction | Boiling point (° C./1 mmHg) | weight (grams) | 1H-NMR signals for CH$_2$ structures of the morpholine ring detectable | inorganic chlorine content (%) |
|---|---|---|---|---|
| 1 | 30-95 | 2 | no | 1.84% |
| 2 | 95-107 | 22.2 | no | 2.08% |

The data indicate the amine hydrochloride salt should be removed, as required in step (ii), before further purification. The mixtures of the isocyanatopropyltrimethoxysilane with high levels of residual amine hydrochloride salt result in the chloride ion reacting with the methoxylsilyl group to form isocyanate containing appreciable amounts of silylchloride groups. Effective removal of the hydrochloride salt through decantation, centrifugation or filtration, is required to minimize the amount of chlorosilyl groups in the purified product. However, the distillation illustrates that the product can be made without the high boiling amine co-distilling with the isocyanatopropyltrimethoxysilane.

Comparative Example F

A one-liter reaction vessel was charged with gamma-aminopropyltrimethoxysilane (150 grams, 0.84 mole), ethyl acetate solvent and dimorpholinodiethylether commercially available from Huntsman as Jeffcat DMDEE (245.3 grams, 1.12 mole). The reaction mixture was cooled to between 0 and 10° C. and phosgene (110.5 grams, 1.13 mol) was added. The reaction mixture was stirred until free of phosgene the batch. Large amounts of a solid amine salts formed, which was filtered from the crude reaction product and washed. The filtrates were concentrated and residual salts occurred which were filtered again. The crude isocyanate had a purity of 75 wt % (GC-ISTD). Other contaminants were 20% dimorpholinodiethylether and 5% impurities. The crude isocyanate was distilled in a thin film evaporator at 135° C./2 mbar. Distillates showed white turbidity with white crystals in the condensation area. The white crystals were sublimed amine-HCl salt. Distilled yield was 90% and the product contained ~5000 ppm Cl.

Comparative Examples G and H

The comparative example G and H were carried out according to the procedures outlined in Comparative Example F, except that the tertiary amine was replaced with one of the amines of Comparative Examples A or B. The results were similar for each Comparative Example G to H as was found for Comparative Example F.

Example 5

Example 5 is carried out according to the procedures outlined in Comparative Example F, except that the tertiary amine is replaced with the tertiary amino-containing compound prepared in Example 3. A viscous mixture (paste-like) of the tertiary amino-containing compound and its salts form, which is easily filtered from the crude reaction product.

The salt is not a fluffy, high melting organic amine hydrochloride salt, and does not fill up the reaction vessel with large amounts of the hydrochloride salts and does not physi-absorb the crude isocyanatopropyltrimethoxysilane, thereby improving the separation of the salt from the crude product in process step (ii). The tertiary amino-containing compound of Example 5 does not co-distill with the isocyanatopropyltrimethoxysilane and does not form white crystals of the amine hydrochloride salt in the distillation column.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for the preparation of an alkoxysilyl group-containing isocyanate compound having the general Formula (I):

$$(R^1O)_{3-a}R^2{}_aSi-R^3-NCO \qquad (I)$$

wherein
each $R^1$ is independently a branched or straight chain alkyl or cycloalkyl group of from 1 to 6 carbon atoms;
each $R^2$ is independently a branched or straight chain alkyl or cycloalkyl group of from 1 to 6 carbon atoms;
$R^3$ is a branched or straight chain alkylene or cycloalkylene group of from 1 to 12 carbon atoms, an arylene group of from 6 to 10 carbon atoms, or an aralkylene group of from 7 to 10 carbon atoms; and
a is 0, 1 or 2 comprising:
(i) reacting ClC(=O)Cl with a corresponding alkoxysilyl group-containing amine having the general Formula (II):

$$(R^1O)_{3-a}R^2{}_aSi-R^3-NH_2 \qquad (II)$$

wherein
each $R^1$ is independently a branched or straight chain alkyl or cycloalkyl group of from 1 to 6 carbon atoms;
each $R^2$ is independently a branched or straight chain alkyl or cycloalkyl group of from 1 to 6 carbon atoms;
$R^3$ is a branched or straight chain alkylene or cycloalkylene group of from 1 to 12 carbon atoms, an arylene group of from 6 to 10 carbon atoms, or an aralkylene group of from 7 to 10 carbon atoms; and
a is 0, 1 or 2,
in the presence of a tertiary amino-containing compound having the general Formula (II):

$$R^4R^5NR^6O-[CH_2CH_2O-]_x[CH_2CH(CH_3)O-]_y[C_4H_8O-]_zR^7-X \qquad (III)$$

wherein
each $R^4$ is independently a straight or branched chain alkyl, cycloalkyl, alkenyl, aryl, aralkyl or arenyl group up to 18 carbon atoms, a heterocarbon group containing from 2 to 18 carbon atoms and at least one oxygen or (—)$_2$NR$^8$ group, wherein $R^8$ is a straight or branched chain alkyl, cycloalkyl, akenyl, aryl, aralkyl or arenyl group from 1 to 10 carbon atoms, or a group in which $R^4$ has a chemical bond with $R^5$ to form a cyclic structure containing the nitrogen atom;
each $R^5$ is independently a straight or branched chain alkyl, cycloalkyl, alkenyl, aryl, aralkyl or arenyl group up to 18 carbon atoms, a heterocarhon group containing from 2 to 18 carbon atoms and at least one oxygen or (—)$_2$NR$^8$ group, wherein $R^8$ is a straight or branched chain alkyl, cycloarkyl, akenyl, aryl, aralkyl or arenyl group from 1 to 10 carbon atoms, or a group in which $R^5$ has a chemical bond with $R^4$ to form a cyclic structure containing the nitrogen atom;
$R^6$ is a straight or branched alkylene group of from 1 to 10 carbon atoms, a cycloalkylene or arylene group of from 5 to 10 carbon atoms, or a —R$^9$C(=O)— group wherein $R^9$ is a straight or branched alkylene group of from 1 to 10 carbon atoms, a cycloalkylene group of from 5 to 10 carbon atoms or an arylene group of from 1 to 10 carbon atoms;
$R^7$ is a straight or branched alkylene group of from 1 to 10 carbon atoms, a cycloalkylene or arylene group of from 5 to 10 carbon atoms, or a —(O=C—)R$^9$— group wherein $R^9$ is a straight or branched alkylene group of from 1 to 10 carbon atoms, a cycloalkylene group of from 5 to 10 carbon atoms or an arylene group of from 1 to 10 carbon atoms;

X is hydrogen or a —NR$^4$R$^5$ group, wherein R$^4$ and R$^5$ have the same meanings as above;

x is 0 to 50;

y is 0 to 50; and z is 0 to 50, with the proviso that the sum of x+y+z is from 2 to 100, to provide for an alkoxysilyl group-containing isocyanate compound;

(ii) separating the hydrochloride salt tertiary amino-containing compound from the alkoxysilyl group-containing isocyanate compound of step (i); and optionally, (iii) purifying the alkoxysilyl group-containing isocyanate of step (ii).

2. The process of claim 1 wherein the alkoxysilyl group-containing amine represented by the general Formula (II) is selected from the group consisting of 3-trimethoxysilylpropylamine, 3-triethoxysilylpropylainine, 3-tributoxysilylpropylamine, 3-tripropoxysilylpropylamine, 1-trimethoxysilylmethylamine, 1-dimethoxymethylsilylmethylamine, 1-diethoxymethylsilylmethylamine, 1-dimethoxymethylsilylpropylamine and 1-diethoxymethylsilylpropylamine.

3. The process of claim 2 wherein the alkoxysilyl group-containing amine represented by the general formula (II) is 3-trimethoxysilylpropylamine.

4. The process of claim 1, wherein the tertiary amino-containing compound is selected from the group consisting of:

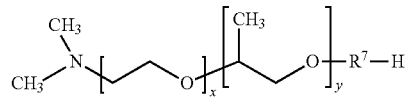
(IV)

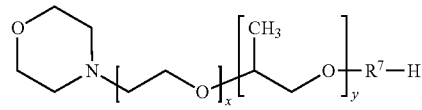
(V)

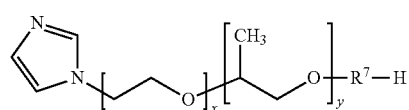
(VI)

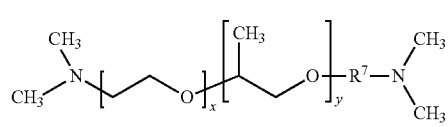
(VII)

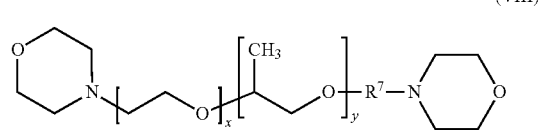
(VIII)

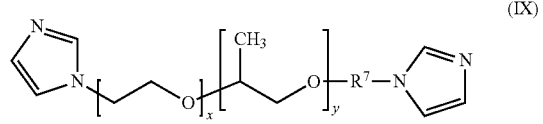
(IX)

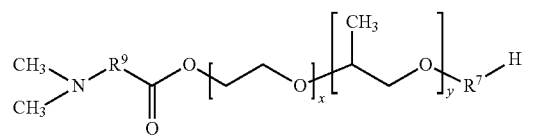
(X)

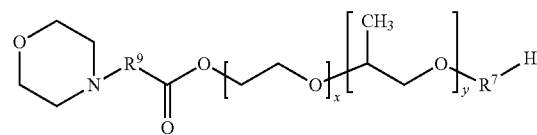
(XI)

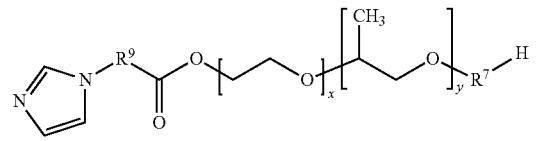
(XII)

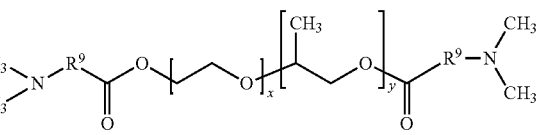
(XIII)

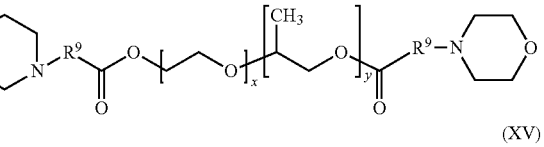
(XIV)

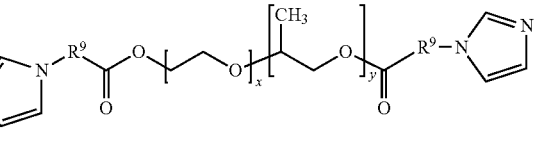
(XV)

wherein in each of formulae (IV)-(XV):

R$^1$ is a straight or branched alkylene group of from 1 to 6 carbon atoms, a cycloalkylene or arylene group of 6 carbon atoms;

R$^9$ is a straight or branched alkylene group of from 1 to 6 carbon atoms, a cycloalkylene or an arylene group of from 6 carbon atoms;

each x and y is independently from 0 to 50, provided that the sum of x and y is from 2 to 100.

5. The process of claim 4, wherein each x and y is independently from 0 to 10.

6. The process of claim 5, wherein each x and y is independently from 3 to 15.

7. The process of claim 4, wherein each R$^7$ and R$^9$ is independently selected from the group consisting of —CH$_2$CH$_2$—, —CH$_2$CH$_2$CH$_2$— and —CH$_2$CH(CH$_3$)—.

8. The process of claim 1 wherein the tertiary a nine-containing compound of step (i) is used at a molar ratio H$_2$N/Cl of from 0.4 to (16.

9. The process of claim 1 wherein the process further comprises using an inert organic solvent in step (i), step (ii), or steps (i) and (ii).

10. The process claim 9 wherein the inert solvent is selected from the group consisting of hydrocarbons, halogenated hydrocarbons, ethers, esters and combinations thereof.

11. The process of claim 1 wherein the reaction is carried out at a temperature of −50° C. to +150° C.

12. The process of claim 1, wherein the composition of step (ii) has a chloride level of less than 1000 parts per million, based on the weight of the alkoxysilyl-containing isocyanate compound.

13. The process of claim 12, wherein the chloride level is less than 100 parts per million, based on the weight of the alkoxysilyl-containing isocyanate compound.

14. The process of claim 1, wherein the alkoxysilyl group-containing isocyanate compound of the general formula (I) is separated from the resulting base hydrochloride salt in step (ii) by decantation, centrifugation or filtration.

15. The process of claim 1, wherein step (iii) is effected in order to provide a purified alkoxysilyl group-containing isocyanate.

16. The process of claim 15, wherein the alkoxysilyl group-containing isocyanate compound of Formula (I) is purified by distillation.

17. The process of claim 16, wherein the alkoxysilyl group-containing isocyanate compound of Formula (I) has a chloride level of less than 100 parts per million, based on the weight of the alkoxysilyl-containing isocyanate compound.

18. A composition comprising an alkoxysilyl group-containing isocyanate compound made by the process of claim 1.

19. The composition of claim 18, wherein the alkoxysilyl group-containing isocyanate compound is selected from the group consisting of 3-isocyanatopropyltrimethoxysilane, 3-isocyanatopropyltriethoxysilane, and 1-isocyanatomethyltrimethoxysilane.

* * * * *